June 6, 1961 E. B. LE GRICE Plant Pat. 2,060
HYBRID TEA-ROSE PLANT
Filed Feb. 26, 1960
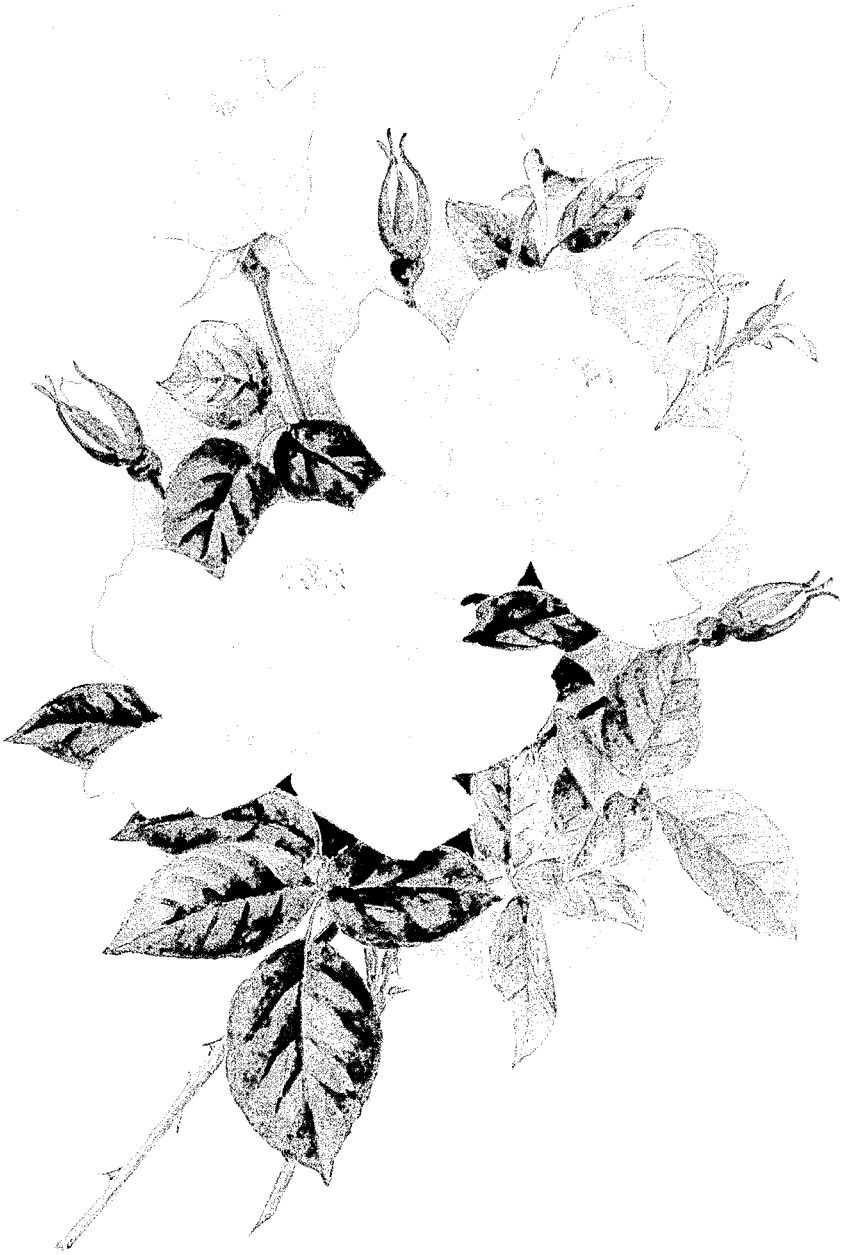
WITNESS
Addison E. Avery
INVENTOR
Edward Burton Le Grice,
by: John H. Leonard,
his ATTY.

United States Patent Office

Plant Pat. 2,060
Patented June 6, 1961

2,060
HYBRID TEA-ROSE PLANT

Edward Burton Le Grice, North Walsham, Norfolk, England

Filed Feb. 26, 1960, Ser. No. 11,391
1 Claim. (Cl. 47—61)

This invention relates to a new variety of hybrid tea-rose plant.

The present rose plant was produced originally by hand crossing under glass an unpatented tea-rose, known commercially as "Wellworth," as a seed parent, with a patented hybrid tea-rose known commercially as "Ellinor Le Grice," Plant Patent No. 917, as the pollen parent.

The pollen parent, "Ellinor Le Grice" was originally produced by a crossing of a hybrid tea-rose, known commercially as "Lilian" with a hybrid tea-rose, known commercially at "Golden Dawn." Neither Lilian nor Golden Dawn is patented.

The new variety was asexually reproduced by me, at my nurseries at North Walsham, England, by budding. The new variety has been tested in England, the United States, and Italy.

The drawing shows in color typical stalks with leaves, buds, blooms and thorns.

The exposed plant is a woody bush of regular contour, symmetrical in outline, with a flattened top. It grows generally upright to a height of about 2½ to 3 feet in from 2½ to 3 years. It is vigorous in growth.

The exposed portion of the plant has a good resistance to low temperature when protected, and has withstood temperatures around zero Fahrenheit unprotected. Its resistance both to drought and wet seasons is good. It has not been attacked by diseases.

For growth of the bush, it prefers moderate sun and a southwest exposure. It thrives well in good loam with normal drainage.

The color references herein used are from the British Colour Council and Royal Horticultural Society Colour Charts.

The main stalks of the plant are upright and slightly branched. They are relatively stiff and are adequate to support the foliage and blooms well.

The new growth of the stalks is a Spinel Red, Chart 189, No. 0023/1 or Fern Green, Chart 186, No. 0862/3.

The old growth is Fern Green, Chart 186, No. 0862/3. On the old growth, the color is relatively uniform, but on the new growth it is mottled.

The main stalks range from about 18 to 30 inches in length, and grow grouped and upwardly. They have a smooth surface texture. The branches of the main stalks are alternately arranged. They are Fern Green, Chart 186, No. 0862/2. They have a smooth surface texture and are relatively stiff and straight.

The foliage in general is open, the leaves being alternately arranged and of medium quantity. The new leaves on the top surface are Spinel Red, Chart 189, No. 0023, or Fern Green, Chart 186, No. 0862/3. Their top surfaces are shiny. On the bottom, the new leaves are the same color as on top, but with a dull finish.

The old leaves, on the top surface, are Spinach Green, Chart 187, No. 0960/3. On the bottom, they are Fern Green comparable to Chart 186, No. 0862.

In general, the color of the old and new leaves is variegated, the variegation comprising Fern Green, Chart 186, No. 0862/2 splashed with Spinel Red, Chart 189, No. 0023 in the case of younger leaves and Spinach Green, Chart 187, No. 0960/3 with Fern Green, Chart 186, No. 0862/3. The leaves have distinct veins and midribs.

The leaves are of medium size, varying from 2½ to 6 inches in length and from 1 to 4 inches in width. They are of the normal shape, being pinnate with serrated margins and with acuminate apices. They are of average thickness. On the upper face, they are smooth and glossy. On the lower face, they are smooth and dull.

Their persistency on the plant is good.

The petioles or leaf stems are Spinel Red, Chart 189, No. 0023. They average in length to about 2½ inches and are quite strong. Their surface texture is very slightly thorny.

The edges and tips of the stipules are Fern Green, Chart 186, No. 0862/3. The centers are Spinel Red, Chart 189, No. 0023.

The plant grows and blooms well throughout all temperate regions. It prefers well drained, neutral, rich loam soil. It prefers sun in a western exposure, and dry and hot seasons.

Under ideal conditions, the flowers are larger and more lasting, their color better, and their quantity greater.

Adequate moisture and warmth results in larger flowers. Excessive heat bleaches the color slightly.

The plant blooms recurrently for a period of about five to six months.

The buds are large, smooth, and slightly globular in shape. They are borne upright on terminals, and sometimes on laterals. Their color when the sepals first divide varies from Naples Yellow, Chart 121, No. 403 to Egyptian Buff, Chart 122, No. 407.

When the petals begin to unfurl, the color varies from Egyptian Buff, Chart 122, No. 407 to Naples Yellow, Chart 121, No. 403. When half blown, the color is Naples Yellow.

The sepals are normal.

The calyx is normal in shape, size, and surface texture.

The peduncles average from 2 to 2½ inches in length.

The pedicels average from 2 to 2½ inches in length and are strong. They have an almost smooth surface texture with a few very small bristles. Their color generally is Fern Green, Chart 186, No. 0862 to 0862/3. They have tiny thorns which are Spinel Red in color, Chart 189, No. 0023.

The blooms open slowly. Cool, wet weather retards development.

The blooms average from 5 to 7 inches in diameter and an average plant will bear about 25 blooms each season. The blooms are borne singly. On the plant, they last about 4 to 6 days, and, when cut, about 4 to 5 days. In each instance, they retain their color. The blooms average about 28 petals each.

The petalage ranges from an Egyptian Buff, Chart 122, No. 407 at the center to Naples Yellow, Chart 121, No. 403 at the outer portion. The base of the petals also is Egyptian Buff. The inside of the petals is Naples Yellow, Chart 121, No. 403. The reverse of the petals is Egyptian Buff, Chart 122, No. 407.

The general tonality of the plant from a distance, when it is in bloom, is an Egyptian Buff, Chart 122, No. 407/2. The buff is more uniform and slightly deeper during the season, varying on Chart 122 from No. 407/3 to 407. There is very little change in color throughout the blooming period.

The petals are thick and strong. On the inside, they are Naples Yellow, Chart 121, No. 403 and on the outside are Egyptian Buff, Chart 122, No. 407. They have the normal arrangement and good persistence on the bloom, both cut and uncut. There are a few petaloids, usually not exceeding two or three.

The buds are very slightly globular and open into regular pointed flowers.

The fragrance of the blooms is of medium strength and honey scented. The fragrance lasts good in both cut and uncut flowers.

The stamens are normal and abundant. In color, they are Lemon Yellow, Chart 4/1. The filaments are of medium size. Their upper parts are Lemon Yellow, Chart 4/1 and their lower parts are Crimson, Chart 22/1. The pollen likewise is Lemon Yellow, as are the styles. The stigmas are Egyptian Buff, Chart 122, No. 407.

The styles are about ¼ of an inch in length. The stigmas are about 1/16 of an inch wide and plentiful.

The fruit is of the usual form and abundance.

The quantity of thorns is moderate. On the laterals and on the main stalk from the base, they are few and hooked, short, and stiff. In color they are Spinel Red, Chart 189, No. 0023. They are evenly distributed on the main stalk and on the laterals. On the peduncles they are reduced to bristles.

The drawing further illustrates the characteristics of the variety and the following tabulation is a detailed description of the new variety:

*General*

Parentage:

*Seed parent.*—"Wellworth," unpatented.

*Pollen parent.*—"Ellinor Le Grice," Plant Patent No. 917, a cross between "Lilian" and "Golden Dawn," both of which latter roses are unpatented.

Classification: Botanic—Rosa.

*Flower*

Blooming habit:

*Location where observations were made.*—North Walsham, England; "Oaklands," St. Albans, England; Bologna, Italy; Mentor, Ohio, U.S.A.

*Flowering.*—Recurrent for about five to six months, from early June until frost.

Bud:

*Size.*—Large.

*Form.*—Slightly globular with smooth aspect.

*Color.*—When sepals first divide, petals vary from Naples Yellow, Chart 121, No. 403 to Egyptian Buff, Chart 122, No. 407; when petals begin to unfurl the color varies from Egyptian Buff to Naples Yellow; and when half blown the color is Naples Yellow.

*Sepals.*—Normal.

*Calyx.*—Normal in shape, size, and surface texture.

*Peduncle.*—From two to two and one half inches in length.

*Pedicles.*—Average two to two and one half inches in length; strong; smooth with few small bristles. Color—Fern Green, Chart 186, No. 0862 to No. 0862/3.

*Opening.*—Slowly, retarded to cool, wet weather.

Bloom:

*Size.*—Five to seven inches in diameter.

*Borne.*—Singly.

*Stems.*—Length two to two and one half inches; strong. Aspect—almost smooth with a few very small bristles. Color—Fern Green with Spinel Red bristles.

*Form.*—When first opened—usual.

*Permanence.*—On the plant—about 4 to 6 days. When cut—about 4 to 5 days.

Petalage:

*Number of petals under normal conditions.*—Twenty-eight.

*Color.*—Egyptian Buff at center and Naples Yellow at outer petals.

*Variegations.*—The color of each petal is the same throughout from base to tip. Inside is Naples Yellow. The reverse is Egyptian Buff.

*Discoloration.*—Color becomes more uniform and slightly deeper as blooming season progresses.

Petals:

*Texture.*—Smooth, thick, and strong.

*Appearance.*—Naples Yellow inside and Egyptian Buff on the reverse.

*Form.*—Slightly recurvent.

*Arrangement.*—Normal.

*Petaloids in center.*—Few, about two or three.

*Persistence.*—Good, uncut and cut.

*Fragrance.*—Medium, honey scented.

*Lasting quality.*—Good, uncut or cut.

Genital organs:

*Stamens.*—Normal. Color—Lemon Yellow, Chart 4/1.

*Filaments.*—Medium. Color—Upper part Lemon Yellow, lower part Crimson, Chart 22/1.

*Pollen.*—Lemon Yellow, Chart 4/1.

*Styles.*—¼ of an inch, colored Crimson, Chart 22/1.

*Stigmas.*—About 1/16 of an inch wide. Color—Egyptian Buff.

*Ovaries.*—Plentiful.

Fruit: Variety and form—usual.

*Plant*

Form: A woody bush, generally upright, symmetrical with flattened top.

Growth: Vigorous but not high, about 2½ feet to 3 feet high at two years.

Foliage: Open.

*Size.*—Medium length from 2½ to 6 inches and width from 1½ to 4 inches.

*Quantity.*—Medium.

*Color.*—New leaves, on top, Spinel Red, Chart 189, No. 0023 or Fern Green, Chart 186, No. 0862/3. Shiny on upper surface, dull on reverse. Old leaves Spinach Green, Chart 187, No. 0960/3 on their under side; old leaves Fern Green, Chart 186, No. 0862 on their top side.

*Shape.*—Normal, pinnate.

*Texture.*—Upper side smooth and glossy, lower face smooth and dull. Average thickness, borne alternately.

*Edge.*—Serrated.

Petiole: Length, about 2½ inches, very slightly thorny; strong. Color—Spinel Red.

Stipules: Fern Green, Chart 186, No. 0862/3 on edges, tips; centers Spinel Red Chart 189, No. 0023.

Wood:

*Newest wood.*—Color—Spinel Red, Chart 189, No. 0023/1 on Fern Green, Chart 186, No. 0862/3.

*Old wood.*—Color—Fern Green, Chart 186, No. 0862/2.

*Bark.*—Smooth.

Thorns:

*Quantity.*—Moderate; on main stalks from base and on laterals, few and hooked.

*Form.*—Short and stiff.

*Position.*—Evenly distributed on main stalks and laterals; and peduncles reduced to bristles.

The most distinctive feature and characteristic of the new hybrid rose plant resides in its uniform creamy yellow color of the blooms combined with well shaped flowers, good foliage and aroma, large flowers and strong upright growth.

It is the general high rating for many qualities combined in a single plant rather than any single quality.

Having shown and described my new variety of hybrid tea-rose plant, and its manner of asexual reproduction, I claim:

The new and distinct variety of hybrid tea-rose plant herein shown and described.

No references cited.